(12) United States Patent
Focia et al.

(10) Patent No.: US 7,940,061 B2
(45) Date of Patent: May 10, 2011

(54) SYSTEMS AND METHODS FOR DETECTING ANOMALIES ON INTERNAL SURFACES OF HOLLOW ELONGATE STRUCTURES USING TIME DOMAIN OR FREQUENCY DOMAIN REFLECTOMETRY

(75) Inventors: Ronald J. Focia, Stevens, PA (US); Charles A. Frost, Albuquerque, NM (US)

(73) Assignee: Profile Technologies, Inc., Manhasset, NY (US)

( * ) Notice: Subject to any disclaimer, the term of this patent is extended or adjusted under 35 U.S.C. 154(b) by 402 days.

(21) Appl. No.: 11/998,544

(22) Filed: Nov. 30, 2007

(65) Prior Publication Data

US 2008/0143344 A1 Jun. 19, 2008

Related U.S. Application Data

(60) Provisional application No. 60/872,225, filed on Nov. 30, 2006.

(51) Int. Cl.
*G01R 27/08* (2006.01)
(52) U.S. Cl. .......................... 324/700; 324/533; 324/642
(58) Field of Classification Search .................. 324/642, 324/700
See application file for complete search history.

(56) References Cited

U.S. PATENT DOCUMENTS

| | | | | |
|---|---|---|---|---|
| 2,698,923 A * | 1/1955 | Edson | ............................ | 333/228 |
| 2,849,683 A * | 8/1958 | Miller | ............................. | 333/1.1 |
| 3,079,552 A * | 2/1963 | Walker | .......................... | 324/632 |
| 4,970,467 A | 11/1990 | Burnett | | |
| 5,189,374 A | 2/1993 | Burnett | | |
| 5,243,294 A | 9/1993 | Burnett | | |
| 5,270,661 A | 12/1993 | Burnett | | |
| 5,719,503 A | 2/1998 | Burnett | | |
| 5,942,687 A * | 8/1999 | Simmonds et al. | ............. | 73/579 |
| 6,020,733 A | 2/2000 | Bradley | | |
| 6,065,348 A | 5/2000 | Burnett | | |
| 6,072,316 A | 6/2000 | Burnett | | |
| 6,078,280 A * | 6/2000 | Perdue et al. | .................. | 342/124 |
| 6,194,902 B1 * | 2/2001 | Kuo et al. | ...................... | 324/637 |
| 6,298,732 B1 | 10/2001 | Burnett | | |
| 6,339,333 B1 | 1/2002 | Kuo | | |
| 6,833,537 B2 * | 12/2004 | Risman et al. | ................ | 219/690 |
| 6,934,655 B2 * | 8/2005 | Jones et al. | ................... | 702/108 |
| 7,196,529 B2 * | 3/2007 | Burnett et al. | ................ | 324/700 |
| 7,642,790 B2 * | 1/2010 | Burnett et al. | ................ | 324/533 |
| 2005/0007121 A1 * | 1/2005 | Burnett et al. | ................ | 324/533 |
| 2008/0308567 A1 * | 12/2008 | Counts-Bradley | ............ | 220/789 |

OTHER PUBLICATIONS

Ishii, T.K., Handbook of Microwave Technology, vol. 1, Components and Devices, Academic Press, 1995, p. 24-27.*

* cited by examiner

*Primary Examiner* — Thomas Valone
(74) *Attorney, Agent, or Firm* — Michael R. Schacht; Schacht Law Office, Inc.

(57) ABSTRACT

Systems and methods for detecting anomalies, such as corrosion, on internal surfaces of hollow elongate bodies, such as pipelines. The pipeline is treated as a circular waveguide, and a fast rise time pulse or a spectrum of electromagnetic waves is launched down the waveguide to perform time domain, or equivalent of time domain (e.g., frequency domain), reflectometry. Anomalies in the internal structure of the pipeline cause reflections which can be measured and related to the physical parameters of the pipeline structure and identified to a particular location.

17 Claims, 4 Drawing Sheets

$H_{11}$  $\lambda_c = 3.412\,a$

SYSTEMS AND METHODS FOR DETECTING ANOMALIES ON INTERNAL SURFACES OF HOLLOW ELONGATE STRUCTURES USING TIME DOMAIN OR FREQUENCY DOMAIN REFLECTOMETRY

RELATED APPLICATIONS

This application claims priority of U.S. Provisional Patent Application Ser. No. 60/872,225 filed Nov. 30, 2006.

TECHNICAL FIELD

The present invention relates to systems and methods for detecting anomalies using time domain reflectometry (TDR) or frequency domain reflectometry (FDR) and, more specifically, to such systems and methods that are adapted to detect anomalies such as corrosion on an inside surface of a hollow elongate member such as a pipe.

BACKGROUND OF THE INVENTION

Corrosion of steel pipes can degrade the structural integrity of the pipeline system. In some pipeline systems, the metallic pipe is insulated with a urethane foam covering and protected by an outer metallic shield. For insulated, shielded pipes, visual inspection for corrosion on the outside of a shielded steel pipe is virtually impossible without physically removing the insulation and outer shield. Corrosion can also occur within a pipe. Visual inspection of the interior of the pipe is also very difficult and is not practically possible when the pipeline is in use.

The need thus exists for improved systems and methods for nondestructively testing for anomalies within a pipe structure.

SUMMARY OF THE INVENTION

The present invention may be embodied as an anomaly detection system for detecting an anomaly on an internal surface of a structure, where the structure is hollow, elongate, and conducting. One example of an anomaly detection system of the present invention comprises an access port, an antenna, a signal source, and a signal analyzer. The access port formed at a location along the structure. The antenna is extended through the access port. The signal source is operatively connected to the antenna and is capable of causing the antenna to transmit a test signal along the structure. The signal analyzer is operatively connected to the antenna to analyze signals received by the antenna in at least one of a time domain and a frequency domain. When the test signal encounters the anomaly, the anomaly causes a reflected signal to be transmitted back towards the antenna.

DETAILED DESCRIPTION OF EXAMPLE EMBODIMENT

The present invention relates to systems and methods for assessing the internal structure of a pipeline. In particular, the systems and methods of the present invention may be used to detect internal corrosion and other defects on pipelines.

Figure 1:
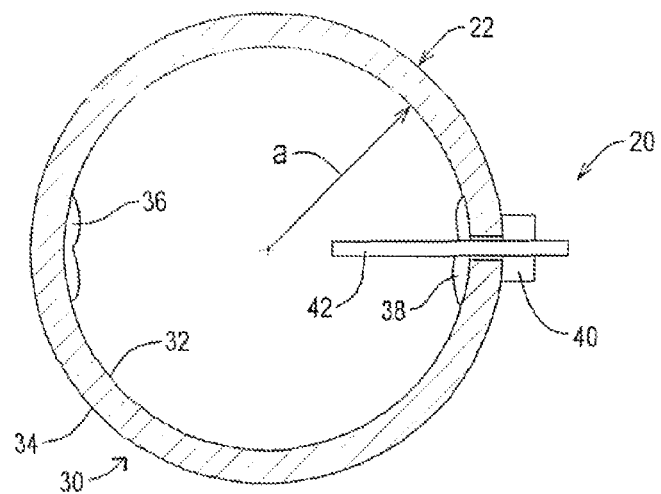
FIG. 1 is a highly schematic view depicting the cross-section of an elongate, conductive member in the form of a pipe, which defines a circular waveguide having a radius "a"
Figure 2:
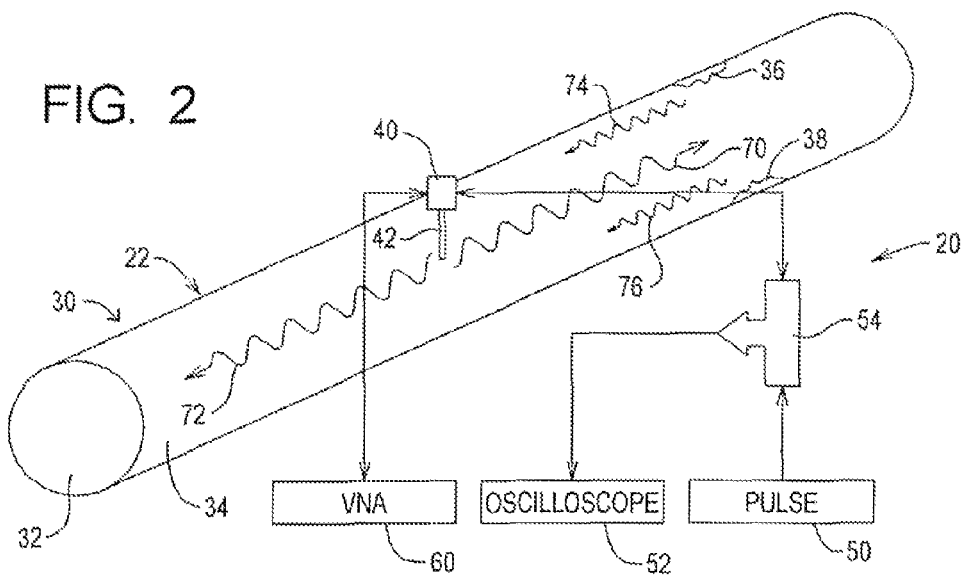
FIG. 2 is a schematic view of a section of a pipeline being tested in accordance with the principles of the present invention.

Referring initially to FIGS. 1 and 2 of the drawing, depicted therein is an example anomaly detection system 20 for detecting anomalies in an elongate, hollow, conductive member 22. The example conductive member 22 is a pipeline comprising a length of pipe 30 having an inner wall 32 and an outer wall 34. The inner wall 32 of the pipe 30 is corroded at locations 36 and 38 as shown in FIGS. 1 and 2. The example pipe 30 is cylindrical and defines a radius "a" as shown in FIG. 1.

An access port 40 is formed in the pipe 30, and one example of such an access port will be described in further detail below. The access port 40 allows an antenna 42 (sometimes referred to as a stub) to be inserted into the interior of the pipe 30. In one example, a pulse generator 50 and oscilloscope 52 are connected to a connector 54 that is in turn connected to the antenna 42. In another example, a vector network analyzer (VNA) capable of generating a test signal and monitoring received signals is connected to the antenna 42. Both test setups are depicted in FIG. 2 for simplicity, but the anomaly detection system 20 can be implemented using either of these two test setups.

In any case, the antenna 42 generates a test signal that propagates in both directions from the access port 40 along the pipe 30 in the form of first and second signals 70 and 72 as shown in FIG. 2. FIG. 2 also shows that, in the example pipe 30, the anomalies 36 and 38 reflect at least a portion of the first test signal 70 back toward the access port 40 in the form of first and second reflected signals 74 and 76. The antenna 42 receives the first and second reflected signals 74 and 76. The first and second reflected signals 74 and 76 are then processed by a signal analyzer such as the oscilloscope 52 and the VNA 60.

While in the example pipe 30 first and second areas of anomaly 36 and 38 cause first and second reflected signals 74 and 76 to be transmitted, the principles of the present invention operate with only one area of anomaly or with more than two areas of anomaly. Additionally, if more than one area of anomaly is present, these areas can be located at the same general location along the length of pipe or can be spaced from each other along the length of pipe.

Analysis of the reflected signals 74 and 76 can be used to determine the presence and location of one or more anomalies along the elongate member 22 or pipe 30.

With the foregoing general discussion of the present invention, a more specific example will now be described.

As will be described in further detail below, these methods are based on the principle of reflectometry, either time domain reflectometry (TDR) or frequency domain reflectometry (FDR). For example, a fast rise time pulse or spectrum of electromagnetic waves may be launched down a transmission line structure, and reflections that occur from changes in the characteristic impedance of the transmission line structure are measured. The magnitude and polarity of any reflections can be related to the physical parameters of the structure and any deviations from nominal.

More specifically, the pipe 30 can be considered a transmission line in the form of a circular waveguide formed by the electrically conducting boundaries of the inner wall 32 of a metallic pipe 30, as shown in FIGS. 1 and 2. A circular waveguide is known to support various propagating wave modes. The dominant mode for a circular waveguide is the $TE_{11}$ mode. However, there are numerous other modes that can propagate in a circular waveguide, e.g. $TM_{01}$, $TE_{01}$, etc., and these modes could also be used for the TDR methods described herein. Additionally, each propagating mode may exhibit a particular inclination to detect different types of defects or have different attenuation characteristics.

For each propagating mode, a circular waveguide such as the pipe 30 presents a particular characteristic impedance. Any deviation in the internal dimensions of the pipe, e.g. primarily from wall loss due to corrosion, will cause a change in the characteristic impedance of the waveguide and result in reflections being observed at the monitoring point.

Thus, to detect anomalies or defects in the internal structure of the pipe 30, propagating modes, in the form of the transmitted waves or signals 70 and 72, are launched down the pipeline 30 from the access port 40 using the antenna 42. The reflected waves or signals 74 and 76 are monitored at the launch point 40 or at other points where a monitoring antenna such as the antenna 42 may be located. It would be particularly beneficial to perform these measurements on newly commissioned pipelines, i.e. perform a baseline measurement, and then perform periodic monitoring. This practice of obtaining a baseline and performing periodic monitoring would significantly increase the sensitivity of the measurement and reduce the minimum detectability threshold for any type of observed defect.

Figure 3:
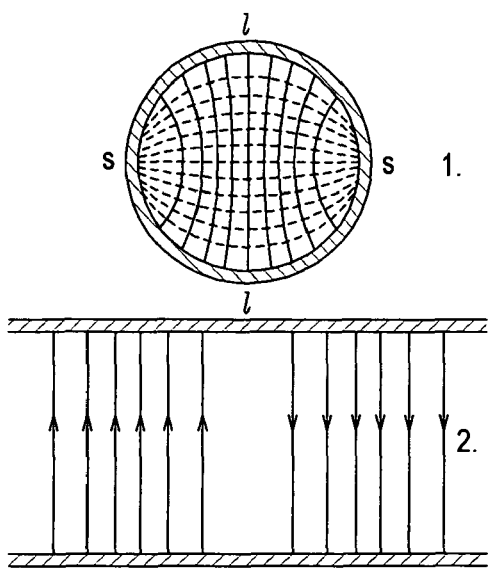
FIG. 3 represents electric (solid lines) and magnetic (dashed lines) fields for the $TE_{11}$ mode of a circular waveguide.
Figure 3:
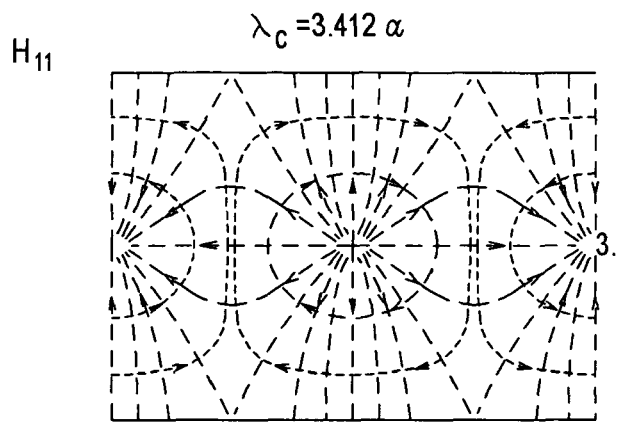

FIG. 3 of the drawing depicts the electric (solid lines) and magnetic (dashed lines) fields for the circular waveguide $TE_{11}$ mode at a given cross-section. The $TE_{11}$ mode can be excited by using a stub antenna (FIG. 1) oriented along the electric field lines for the mode. Thus, launching waves down the circular waveguide requires at least one access port such as the port 40 described above. The access port or ports 40 will need to be engineered for the particular pipeline, fluid, and pressure to be contained.

If a plurality of the ports 40 are used, the spacing of the access ports 40 could, as will be described below, be on the order of several thousand feet. The antennas used to excite particular modes could be left in place, if they are not affected by or affect the fluid flow, and periodic monitoring could be performed without shutting down the pipeline. The shape of the antenna required to excite the various other propagating modes supported by the waveguide will differ from that used for the $TE_{11}$ mode.

Figure 4:
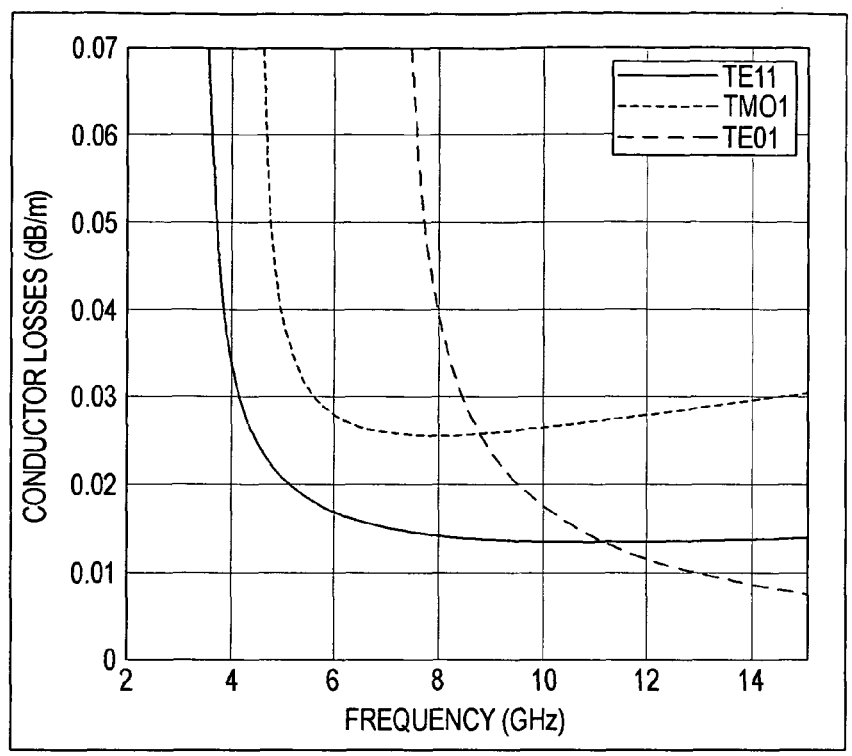
FIG. 4 represents conductor losses versus frequency for the first three propagating modes in an air-filled, copper circular waveguide with a diameter of 2 inches.

Any propagating waves or test signals launched down the inside of a pipeline will suffer attenuation as they propagate and thus decrease in amplitude. A typical attenuation curve for various modes in a circular copper waveguide is shown in FIG. 4. The exact attenuation factor for a particular mode will depend on the physical parameters of the system, e.g. the conductivity of the steel used for the pipe and the dielectric properties of the fluid contained within the pipe such as natural gas or crude oil. For the dominant $TE_{11}$ mode in the waveguide of FIG. 3, a ~3 dB attenuation will occur after ~100 meters (~328 feet). With good measurement techniques, using equipment with a large dynamic range, and averaging multiple acquisitions, a system constructed in accordance with the principles of the present invention could tolerate attenuation on the order of ~20 dB or more. Thus, distances between monitoring locations on the order of ~600 meters (~2000 feet) or larger could be possible.

As generally described above, the equipment used for this method could be comprised of the pulse generator 50, the oscilloscope 52, and the resistive voltage divider or connector 54 or a vector network analyzer (VNA) 60. The use of this equipment to implement systems and methods for analyzing pipeline using TDR methods is generally known. A fast rise time pulse generator and oscilloscope would be used to perform traditional TDR. The VNA would be used to perform equivalent-time TDR using specific frequencies and then converting the frequency domain results to the time domain.

The antennas 42 used to excite the circular waveguide modes could be engineered to isolate them from the fluid contained in the pipeline, i.e. they could be coated with a dielectric, and the access ports could be engineered to allow for easy connection. The complexity of the antennas 42 and access ports 40 would be determined by the pipeline system they are to be installed on. The allowable voltage and field magnitudes must be determined so as not to adversely affect the system to be monitored.

Wall loss due to corrosion is a case where the dominant mode of a signal is expected to survive and propagate past the defect. However, the impedance of the waveguide structure will change at the location where the defect is located and cause a reflection to be observed in the measured waveform. The wave speed of the particular mode used can be estimated from the physical parameters of the pipeline and fluid in it, or calibrations can be performed to measure the actual wave speed. Thus, any defects measured versus time can be related to a distance from the monitoring point. This method should also be able to detect other defects or abnormalities in a pipeline, for example, crushing of the pipe, water in the pipe, and/or sludge buildup in the pipe.

The present invention thus allows the internal structure of a metallic pipeline to be assessed while the pipeline is in operation. In this invention, the electrically conducting boundaries of the inner wall 32 of the metallic pipe 30 form a circular waveguide, and traditional or equivalent-time TDR is used to locate defects in the internal structure of the pipeline.

Access ports and antennas may be installed at one or more locations along a pipeline. The antennas could be permanently or temporarily inserted into the pipeline and then connected to an external source. Such antennas could be shaped and oriented such that they excite the desired propagating modes in the pipeline.

The external source could consist of a fast rise time pulse generator for traditional TDR or a vector network analyzer (VNA) for equivalent-time TDR. The transmitted and reflected waves are monitored using an oscilloscope or VNA. Any defects in the internal structure of the pipeline cause reflections from the transmitted signal, and these reflections are monitored at the feed point 40 or at other points where antennas 42 are located on the pipeline.

The nature of the defects is related to the physical parameters of the pipeline and the fluid it contains. The locations of the defects are identified using a calculated or calibrated velocity factor for the propagating circular waveguide mode used.

Circular waveguides used for communications purposes are normally fabricated from copper or electroplated on the inner surface with a metal having a high electrical conductivity, such as silver or gold. This structure is used to minimize the wave attenuation due to conductor losses and promote long propagation distances.

The conductor losses $\alpha_c$ for the transverse electric (TE) modes in a circular waveguide are governed by the equation $$\alpha_c = \frac{R_s}{ak\eta\beta}\left(k_c^2 + \frac{k^2}{p'^2_{nm}-1}\right), \qquad (A1)$$

where $R_s$ is the surface resistance of the conductor, a is the radius of the waveguide, k is the wavenumber, $\eta=\sqrt{\mu/\in}$ is the wave impedance, $\beta$ is the propagation constant of the mode, $k_c$ is the cutoff wavenumber of the mode, and $p'_{nm}$ is the $m^{th}$ root of the derivative of the Bessel function of the first kind, i.e. $J'_n(p'_{nm})=0$ (see, e.g., David M. Pozar, *Microwave Engineering*, 3rd Ed., John Wiley & Sons, Inc., New Jersey (2005).

The surface resistance $R_s$ of the metal conductor is related to the frequency of the mode f and the electrical conductivity $\sigma$ of the metal conductor lining the surface of the waveguide and is given by $$R_S = \sqrt{\frac{\omega\mu_o}{2\sigma}}, \qquad (A2)$$

where $\omega=2\pi f$ and $\mu_o=4\pi\times 10^{-7}$ H/m is the permeability of free space.

The wavenumber k is given by $$k=\omega\sqrt{\mu\in}, \qquad (A3)$$

where $\mu$ and $\in$ are, respectively, the permeability and permittivity of the medium filling the waveguide. The cutoff wavenumber of the mode $k_c$ is given by $$k_c = \frac{p'_{nm}}{a}. \qquad (A4)$$

The propagation constant of the mode $\beta$ is given by $$\beta=\sqrt{k^2-k_c^2}. \qquad (A5)$$

The above equations completely describe wave attenuation related to conductor losses for the TE modes. Similar equations exist for the transverse magnetic (TM) propagating modes.

If the waveguide is filled with a medium other than free space, the propagating wave modes will also suffer from attenuation due to dielectric losses. The attenuation due to dielectric loss is given by $$\alpha_d = \frac{k^2 \tan\delta}{2\beta}, \qquad (A6)$$

where tan $\delta$ is the loss tangent of the dielectric material filling the waveguide. The total attenuation will be the sum of the conductor and dielectric attenuation and is given by $$\alpha=\alpha_c+\alpha_d. \qquad (A6)$$

In practice, the dielectric losses are usually much larger than the conductor losses and will dominate the attenuation of the propagating waveguide modes.

The conductor loss characteristics for the first three propagating waveguide modes in a small diameter (2 inch), air-filled, copper circular waveguide are shown in FIG. 4. The loss characteristics are illustrated since detection of anomalies using time or frequency domain reflectometry will involve measuring reflected signals and these signals must be above the minimum detectability of the instrument used for the measurement. How well the measurement instrument can handle attenuation will determine the distance range of anomaly detection. For example, if the measurement technique has a tolerable round-trip attenuation of 20 dB using the $TE_{11}$ mode (at $\alpha_c \approx 0.02$ dB/m), wave injection and monitoring probes may be placed in the 2 inch diameter air-filled copper waveguide at intervals of approximately 500 meters or every 1600 feet.

Pipelines used for the transport of materials such as natural gas and crude oil are typically fabricated from carbon steel and have a larger diameter than communications waveguides. The electrical conductivity of carbon steel is on the order of $\sigma \approx 5\times10^6$ S/, which is approximately an order of magnitude less than that of copper.

Figure 5:
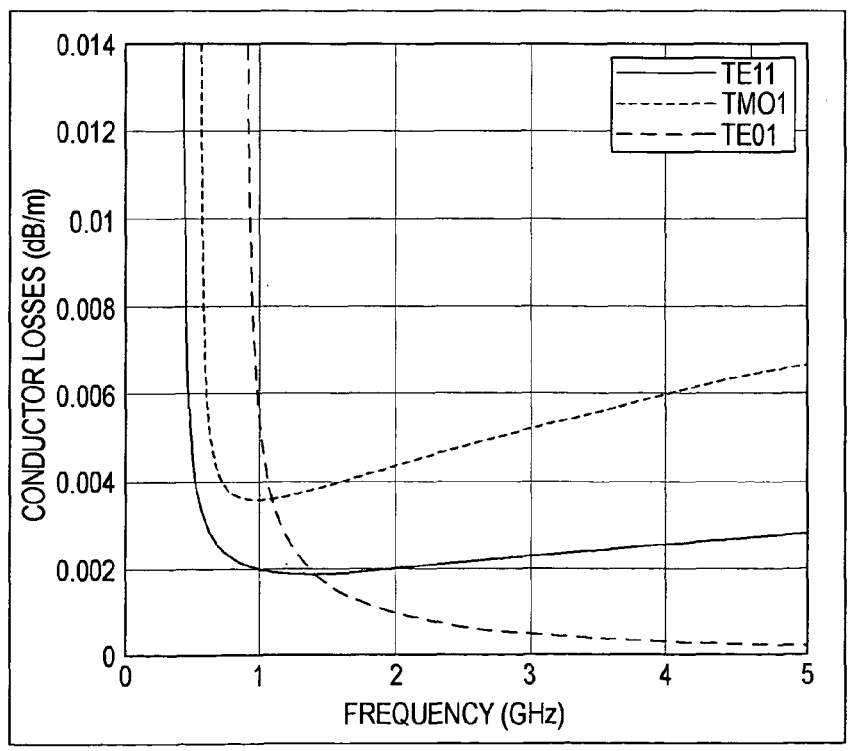
FIG. 5 represents conductor losses versus frequency for the first three propagating modes in an air-filled, carbon steel circular waveguide with a diameter of 16 inches.

FIG. 5 contains a graph showing the conductor loss characteristics of a 16 inch air-filled carbon steel pipe used as a circular waveguide. FIG. 5 illustrates that the losses are significantly lower in the carbon steel pipe. This is due to the larger diameter even though the electrical conductivity is lower. For any given circular waveguide, larger diameters will have lower conductor losses than smaller diameters and thus support farther propagation distances. For the same tolerable round-trip attenuation of 20 dB using the $TE_{11}$ mode (at $\alpha_c \approx 0.002$ dB/m), wave injection and monitoring probes may be placed in the 16 inch diameter air-filled carbon steel waveguide at intervals of approximately 5000 meters or every 16000 feet.

Ultimately, the distance between periodic wave injection and monitoring probes or the detection range to any anomaly will be governed by the type and magnitude of the anomaly and the resolution and dynamic range of the instrument used to measure the return signals. A conservative estimate for the 16 inch air-filled carbon steel pipe used as a waveguide would be that a 3 dB round trip attenuation factor would allow for the detection of small anomalies and would result in a detection range of approximately 2400 feet.

Considering the loss or attenuation associated with a dielectric material allows the measurements outlined in this patent to be performed on a pipeline carrying a liquid or gas without taking the pipeline out of service. There currently exists a commercially available means to "hot tap" access ports into active, pressurized pipelines. The wave injection and monitoring antennae used for the methods described herein can be pressure sealed and incorporated into the commercially available hot tap methods, thus negating the need to depressurize and drain an active pipeline to perform measurements. Alternately, once wave injection and monitoring antennae are installed, an active pipeline may be continuously monitored for anomalies developing over time or transient "events." In particular, the antenna is caused to transmit a test signal such that the test signal is continuously sent. Similarly, the reflected signal is continuously analyzed.

The loss and attenuation associated with the dielectric material filling the pipeline may significantly reduce detection ranges. For example, at microwave frequencies, crude oil exhibits a dielectric attenuation of $\alpha_d \approx 0.05$-$0.07$ dB/cm which is a few orders of magnitude larger than the conductor losses (see, e.g., Viacheslav V. Meriakri, "Millmeter Wave Aquametry," Mat. Res. Soc. Symp. Vol. 631E © 2000 Materials Research Society). This in turn will translate to a few orders of magnitude less in detection range. Although dielectric property data could not be found on natural gas, the Applicant believes that the dielectric attenuation of natural gas is less than that of crude oil due to its lower density and lower water content. If so, the Applicant believes that long detection ranges would still be possible in a pressurized natural gas pipeline.

The dielectric loss and attenuation may not be a detriment to the implementation of the systems and methods of the present invention if the techniques described herein are used to detect transient events. For example, the technique may be used to continuously monitor for water content in a fluid stream as increased water content will significantly change the dielectric properties within the waveguide. The systems and methods of the present invention could also be used to monitor for water slugs moving through a steam or natural gas pipeline, which could result in a potentially dangerous situation. Thus, for example, the system and methods described herein could be used as an early warning system for steam pipelines.

Referring now for a moment to the type of antenna used by systems and methods of the present invention, the antenna used to excite a particular mode will be a straight stub or curved loop depending on which mode is to be excited. The goal of an antenna suitable for use by the systems and methods of the present invention is to orient itself along a particular electric (E) or magnetic (H) field so that the fields generated by the antenna couple into the field lines for the particular waveguide mode.

There are several reasons why different modes may be used to detect different types of anomalies. Some modes exhibit lower loss than others and thus would result in longer detection ranges. The surface currents that drive the propagating waveguide modes are different for the various modes. As such, one mode may be used to detect a purely dielectric anomaly, such as water lying in a low point of a pipeline or plaque buildup, and another mode may be used to detect longitudinal stress cracks that disrupt surface currents.

Figure 6:
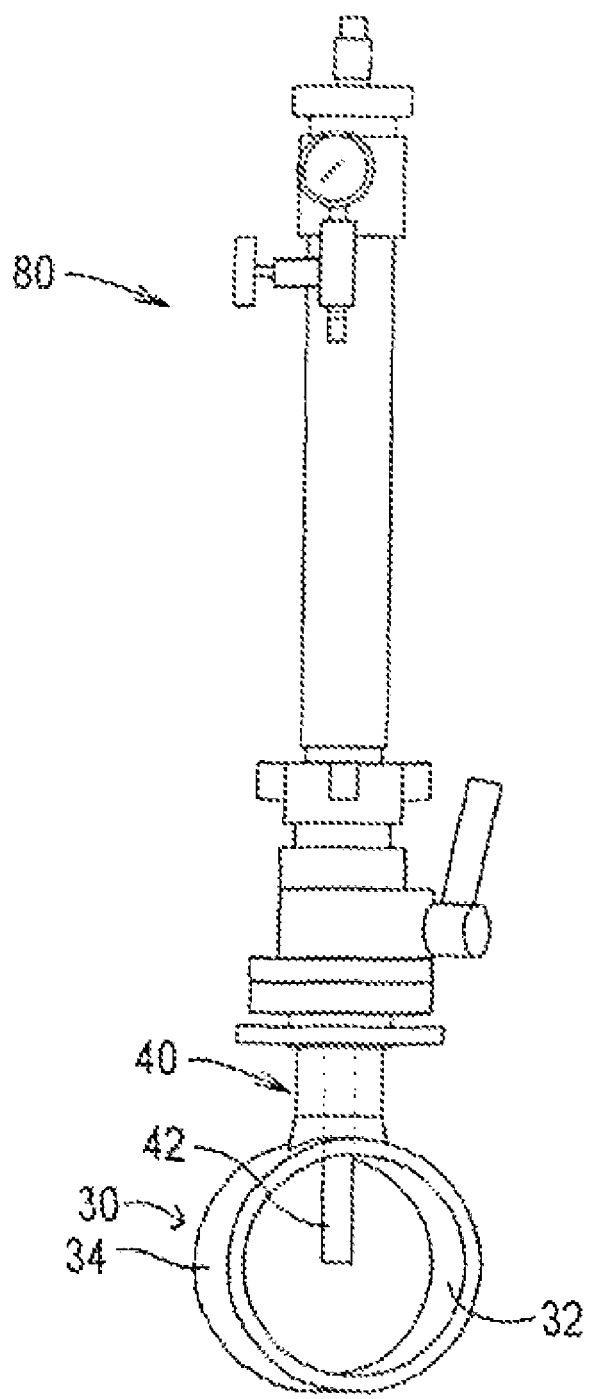
FIG. 6 illustrates an example of a device for allowing access to operating pipelines.

FIG. 6 depicts an example pipeline access system 80 that one could use to hot tap into a pipeline. The example access system 80 is commonly referred to as the Cosasco "hot tap" access method, and more information about this access method can be found at www.rohrbackcosasco.com.

Referring again to FIG. 2, the particular uses of the equipment or test setups depicted therein to perform the measurements of the present invention will now be described. For smaller pipe diameters, where the waveguide cutoff frequencies are higher, a vector network analyzer (VNA) would be used to perform frequency domain reflectometry (FDR). For larger pipe diameters where the waveguide cutoff frequencies are lower, a pulse generator and oscilloscope would be used to perform conventional time domain reflectometry (TDR).

For each detection method, i.e. FDR or TDR, a spectrum of waves is launched from a particular location. Anomalies in the pipeline present impedance changes to the incident propagating waves and thus cause reflections occur. The reflected waves are measured at the injection point, or at other locations, and their magnitude and polarity can be related to the change in the wave impedance. The change in the wave impedance can ultimately be related to changes in the internal structure of the pipeline.

A differentiating B-dot sensor (i.e. a sensor that responds to the time varying magnetic field) could be placed at the wave injection and/or monitoring location to determine the direction from which reflections are occurring without the need to bore multiple access ports to determine the same information by phased array methods. The B-dot sensor is generally a conducting loop oriented so as to encompass magnetic field lines as shown in the field diagrams for the respective modes.

What is claimed is:

1. An anomaly detection system for detecting an anomaly on an internal surface of a metallic pipe structure, where the pipe structure is hollow, elongate, and conducting, the anomaly detection system comprising:
    an access port formed at least one location along the pipe structure, where the access port allows physical access to an interior of the pipe structure;
    an antenna extending into the interior of the pipe structure through the access port;
    a signal source operatively connected to the antenna, where the signal source is capable of causing the antenna to transmit a test signal along the pipe structure; and
    a signal analyzer operatively connected to the antenna, where the signal analyzer analyzes signals received by the antenna in a frequency domain; wherein
    when the test signal encounters the anomaly, the anomaly causes a reflected signal to be transmitted back towards the antenna.

2. An anomaly detection system as recited in claim 1, in which the signal source is a vector network analyzer.

3. An anomaly detection system as recited in claim 2, in which the signal analyzer is the vector network analyzer.

4. An anomaly detection system as recited in claim 1, in which the antenna is oriented along electric field lines defined by the pipe structure.

5. An anomaly detection system as recited in claim 1, in which the antenna is oriented along magnetic field lines defined by the pipe structure.

6. An anomaly detection system as recited in claim 1, in which a propagating mode of the test signal is at least one of the $TE_{11}$ mode and the $TM_{01}$ mode.

7. An anomaly detection system as recited in claim 1, in which a propagating mode of the test signal is selected based on characteristics of at least one of the anomaly, the pipe structure, and fluid within the pipe structure.

8. An anomaly detection system as recited in claim 1, in which the signal analyzer compares the reflected signal with a baseline signal.

9. An anomaly detection system as recited in claim 1, in which the antenna is coated with a dielectric material.

10. An anomaly detection system as recited in claim 1, in which allowable voltage and field magnitudes associated with the test signal are selected to reduce adverse affects on the pipe structure and fluid within the pipe structure.

11. An anomaly detection system as recited in claim 1, further comprising a sensor capable of ascertaining a direction of travel of the reflected signal.

12. An anomaly detection system as recited in claim 1, further comprising a pipeline access system arranged at the access port, where the pipeline access system allows the antenna to be used while pressurized fluid is flowing through the pipe structure.

13. An anomaly detection system as recited in claim 1, further comprising a pipeline access system arranged at the access port, where the pipeline access system allows the antenna to be used when fluid is drained from the pipe structure.

14. An anomaly detection system as recited in claim 1, in which the pipe structure is cylindrical.

15. A method of detecting an anomaly on an internal surface of a metallic pipe structure, where the pipe structure is hollow, elongate, and conducting, the method comprising the steps of:
    forming at least one access port formed at least one location along the pipe structure, where the access port allows physical access to an interior of the pipe structure;

extending an antenna into the interior of the pipe structure through the access port;

causing the antenna to transmit a test signal along the pipe structure, where, when the test signal encounters the anomaly, the anomaly causes a reflected signal to be transmitted back towards the antenna; and analyzing the reflected signal received by the antenna in a frequency domain.

16. A method as recited in claim 15, in which;

causing the antenna to transmit a test signal comprises the step of sending the test signal continuously; and the step of analyzing the reflected signal comprises the step of continuously analyzing the test signal.

17. An anomaly detection system for detecting an anomaly on an internal surface of a hollow, elongate, metallic pipe, comprising:

an access port formed at least one location along the pipe, where the access port allows physical access to an interior of the pipe;

an antenna extending into the interior of the pipe through the access port;

a signal source operatively connected to the antenna, where the signal source is capable of causing the antenna to transmit a test signal along the pipe; and a signal analyzer operatively connected to the antenna, where the signal analyzer analyzes signals received by the antenna in a frequency domain; wherein when the test signal encounters the anomaly, the anomaly causes a reflected signal to be transmitted back towards the antenna.

\* \* \* \* \*